(12) United States Patent
Mizutani

(10) Patent No.: US 6,210,385 B1
(45) Date of Patent: Apr. 3, 2001

(54) ABSORBENT ARTICLE

(75) Inventor: Satoshi Mizutani, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/295,007

(22) Filed: Apr. 20, 1999

(30) Foreign Application Priority Data

Apr. 20, 1998 (JP) .................................................. 10-109961

(51) Int. Cl.[7] .................................................. A61F 13/15
(52) U.S. Cl. .................. 604/385.01; 604/385.04; 604/385.28; 604/385.201
(58) Field of Search .................. 604/385.01, 385.201, 604/385.04, 385.28

(56) References Cited

U.S. PATENT DOCUMENTS

| | | | |
|---|---|---|---|
| Re. 31,922 | * 6/1985 | Mesek et al. | 604/385 |
| 3,710,797 | * 1/1973 | Marsan | 128/284 |
| 3,877,432 | * 4/1975 | Gellert | 128/287 |
| 4,354,901 | * 10/1982 | Kopolow | 162/158 |
| 4,551,142 | * 11/1985 | Kopolow | 604/368 |
| 4,676,787 | * 6/1987 | Sergeant | 604/384 |
| 4,781,712 | * 11/1988 | Barabino et al. | 604/385.1 |
| 4,938,754 | * 7/1990 | Mesek | 604/385.2 |
| 5,569,228 | * 10/1996 | Byrd et al. | 604/385.1 |
| 5,609,588 | * 3/1997 | DiPalma et al. | 604/369 |
| 5,613,961 | * 3/1997 | DiPalma et al. | 604/369 |
| 5,864,890 | * 2/1999 | Niedermeyer | 2/403 |

* cited by examiner

Primary Examiner—John G. Weiss
Assistant Examiner—Paul Shanoski
(74) Attorney, Agent, or Firm—Baker & Daniels

(57) ABSTRACT

A absorbent article such as a sanitary napkin includes an absorbent means and deformation inducing means underlying the absorbent means, and is provided in a direction of its longitudinal center line with deformation guiding means serving for the absorbent means and the deformation inducing means, and thereby improves fitting to a wearer's skin.

11 Claims, 3 Drawing Sheets

ABSORBENT ARTICLE

BACKGROUND OF THE INVENTION

The present invention relates to a disposable absorbent article and more particularly to a sanitary napkin adapted to absorb and contain menstrual discharge, a pad adapted to absorb and contain urine for women suffering from incontinence and the like.

In general, conventional sanitary napkins comprise the absorbent laminate which comprises, in turn, a liquid-pervious topsheet, a liquid-impervious backsheet and a liquid-absorbent core disposed between these two sheets. Japanese Patent Application Disclosure Gazette No. Hei2-11138 discloses a sanitary napkin adapted to be convexly deformed towards a wearer's skin by a deformation inducing element having a flexural resistance and underlying the liquid-absorbent core.

According to the disclosure of Japanese Patent Application Disclosure Gazette No. Hei2-11138, the convex deformation occurs merely in accordance with a previously given convex shape of the deformation inducing element. The sanitary napkin of this type will be compressed in a direction of its thickness during operation of packaging to alleviate its bulkiness. If the napkin remains packaged for a long period until it is unwrapped for its actual use, a compressive restoring force of the deformation inducing element may be deteriorated and it may be impossible to obtain a desired convex deformation. While this drawback may be compensated by properly selecting the material for the deformation inducing element, such proper selection is not necessarily easy.

SUMMARY OF THE INVENTION

In view of the problem as has been described above, it is an object of the present invention to provide a sanitary napkin adapted to eliminate the foregoing drawbacks.

According to the present invention, by a substantially flat and elongate absorbent article having a longitudinal center line, a transverse center line being orthogonal to the longitudinal center line, a body-facing side and a garment-facing side, wherein:

the article includes absorbent means and deformation inducing means lying adjacent said garment-facing side and causing the absorbent means to be convexly deformed towards the body-facing side; the deformation inducing means includes a hydrophobic panel member having a Gurley stiffness value of at least 100 mg; and a convexly deformable zone of the absorbent means and the panel member includes first deformation guiding means formed on the garment-facing side so as to lie on transversely opposite sides of the absorbent means symmetrically with respect to the longitudinal center line and, in the convexly deformable zone, to extend along the longitudinal center line.

When the absorbent article according to the present invention is worn by a wearer, the absorbent means is convexly deformed towards the body-facing side and placed closely against the wearer's external genital organs under the lifting effect of the hydrophobic panel member serving as the deformation inducing means.

DETAILED DESCRIPTION OF THE PREFERRED EMBODIMENTS

Details of an absorbent article according to the present invention will be more fully understood from the description given hereunder based on a sanitary napkin with reference to the accompanying drawings.

Figure 1:
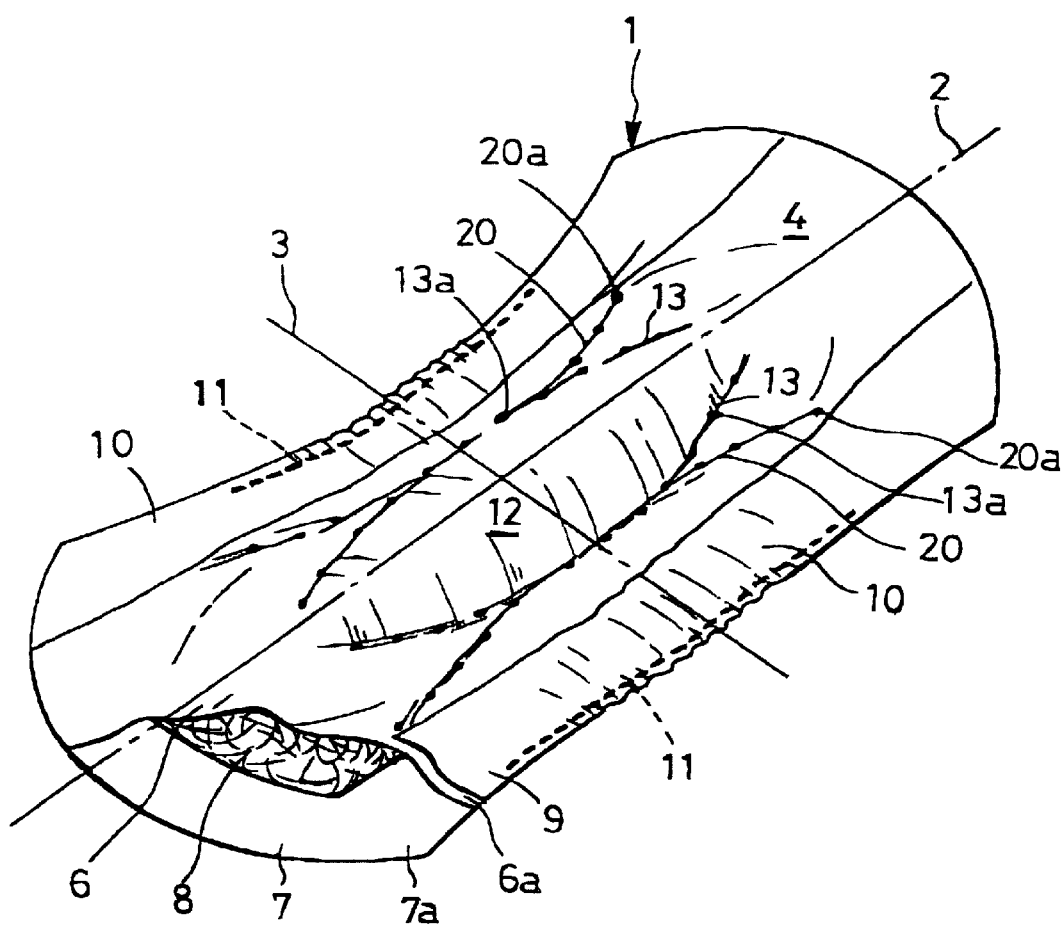
FIG. 1 is a perspective view of an absorbent article according to the present invention in the form of a sanitary napkin, showing a back side thereof as partially broken away.
Figure 2:
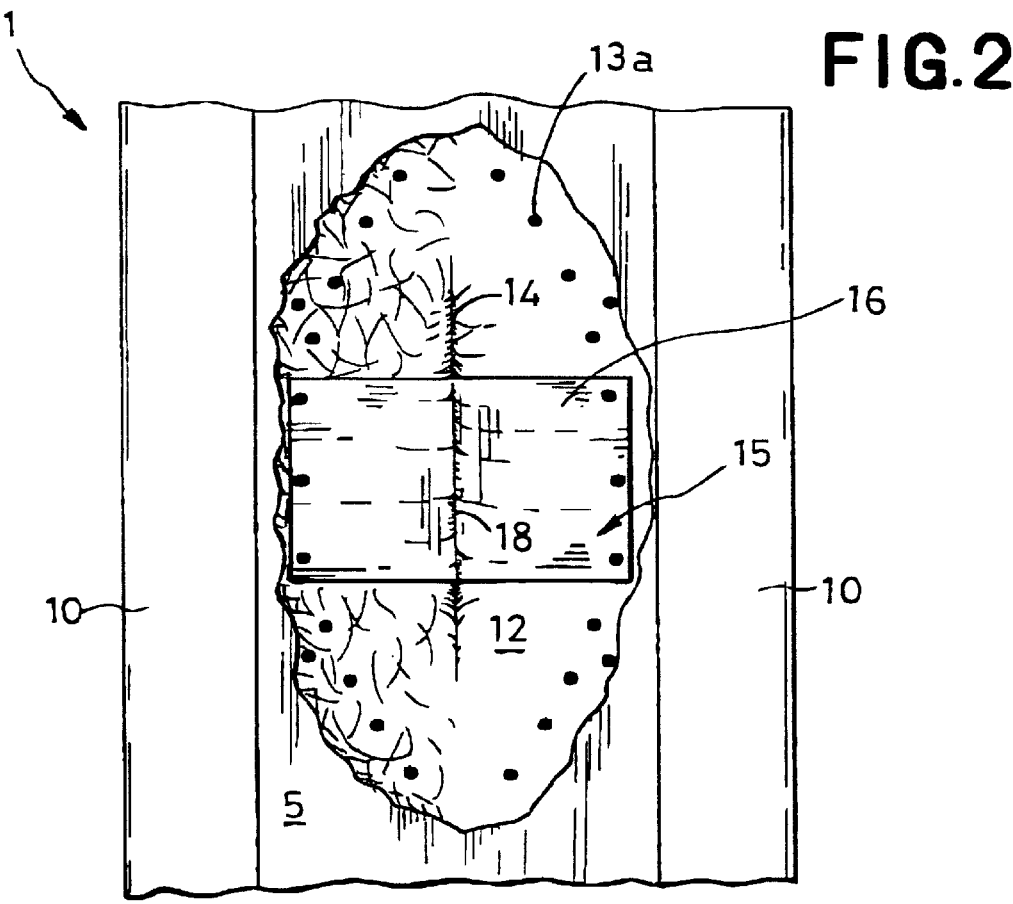
FIG. 2 is a plan view showing the back side of the napkin as partially broken away.
Figure 3:
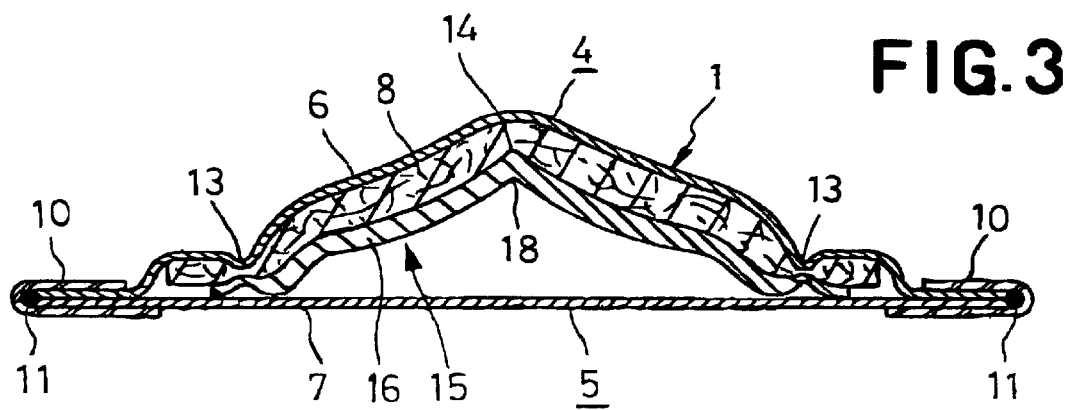
FIG. 3 is a schematic view showing the napkin in its cross-section.

Referring to FIGS. 1–3, a sanitary napkin comprises absorbent means 1. The absorbent means 1 is geometrically defined by a longitudinal center line 2, a transverse center line 3 being orthogonal to the longitudinal center line 2, a body-facing side 4 and a garment-facing side 5. The absorbent means 1 comprises a liquid-pervious topsheet 6, a liquid-impervious backsheet 7 and a liquid-absorbent core 8 disposed between the topsheet 6 and the backsheet 7. The topsheet 6 and the backsheet 7 have their sizes larger than the core 8 in length and width and extending outwards beyond a peripheral edge of the core 8. Along each of transversely opposite sides of the napkin, a side flap 10 is defined by lateral extensions 6a, 7a of the topsheet 6 and the backsheet 7 and longitudinally narrow sheets 9 each folded in two so as to sandwich the lateral extensions 6a, 7a. The side flap 10 is elasticized by an elastic member 11 provided within its outer edge under appropriate tension in its longitudinal direction and adapted to rise (towards a wearer's skin) as the elastic member 11 contracts.

The topsheet 6, the backsheet 7 and the core 8 may be made of materials well known in the field of sanitary napkin and disposable diaper. The topsheet 6 is made of, for example, a hydrophilic or hydrophobic nonwoven fabric, a plastic film having a plurality of apertures, or a laminate consisting of these materials. The backsheet 7 is made of, a moisture-pervious plastic film or a laminate consisting of such plastic film and hydrophobic nonwoven fabric. The core 8 is made of, for example, a mixture of fluff pulp and superabsorptive polymer particles. As a result, both the topsheet 6 and the backsheet 7 are noticeably flexible while the core 8 is semi-rigid. Though not shown, the topsheet 6 is preferably formed over its entire area with a plurality of liquid guiding having larger diameters and therefore a liquid guiding efficiency in a convexly deformable zone 12 as will be described later than in the remaining area of the topsheet 6. The topsheet 6, if it is of nonwoven-fabric-based, preferably contains thermoplastic fibers at least by an amount required for heat-sealing. The core 8 also may contain thermoplastic fibers, if necessary, so far as a desired absorptivity of the core 8 is not affected thereby. The narrow sheet 9 is made of, for example, a hydrophobic nonwoven fabric or a plastic film. The elastic member 11 is made of, for example, natural rubber, synthetic rubber or spandex.

In a region of the absorbent means 1 which is central longitudinally as well as transversely thereof, there are provided a pair of deformation guiding means 13, 13 describing a pair of lines extending longitudinally of the absorbent means 1 and curved outwards symmetrically about a longitudinal center line 2 to define a convexly deformable zone 12 and another pair of deformation guiding means 20 extending also longitudinally of the absorbent means 1 partially in contact with outer sides of the deformation guiding means 13 and curved inwards symmetrically about the center line 2. These deformation guiding means 13, 20 may comprise groups of compressed points (embosses) 13a, 20a or compressed streaks. The absorbent means 1 further includes a single line of deformation guiding means 14 extending on a bottom side (i.e., on the garment-facing side 5) of the core 8 along the longitudinal center line 2 in the convexly deformable zone 12. The deformation guiding means 14 may comprise a single compressed streak or a slit or a group of compressed points (embosses) which divides the core 8 in right and left halves. In the middle of the convexly deformable zone 12, deformation inducing means 15 is secured to a bottom side (i.e., the garment-facing side 5) of the core 8 by means of a hydrophobic adhesive agent such as hot melt adhesive of well known art. The deformation inducing means 15 comprises a rectangular hydrophobic panel member 16. The panel member 16 is substantially deformable to a flat state and has a central zone 18 along the longitudinal center line 2, the central zone 18 normally tending to bend towards the body-facing side 4 (forming so-called latent fold). The central zone 18 of the panel member 16 coincides with the compressed streak 14 serving as the deformation guiding means for the core 8. This central zone 18 preferably comprises a compressed streak having the same shape as the compressed streak 14 and integrally underlying the compressed streak 14. As the napkin is placed against the wearer's external genital organs, the panel member 16 follows a contour of the external genital organs under pressure exerted by the garment and is convexly deformed around the central zone 18 towards the body-facing side 4. In the covexly deformable zone 12, the core 8 is convexly deformed upwards (towards the body-facing side) around the compressed streak 14 serving as the deformation guiding means together with the topsheet 6 under lifting effect due to the deformation of the panel member 16. The deformation causes the core 8 to be spaced from a surface of the backsheet opposed to the core 8 in the convexly deformable zone 12 so that, in the convexly deformable zone 12, the body-facing side 4 may be placed closely against the wearer's external genital organs and leakage of menstrual discharge may be thereby effectively prevented.

Transversely opposite side edges of the panel member 16 extend outwards slightly beyond the deformation guiding means 13, 13 and bonded to the core 8 in proximity of transversely opposite side edges thereof utilizing the groups of compressed points (emboss-heat-sealing points) 13a. To achieve this bonding, the heat-sealing technique may be replaced by use of hot melt adhesive means.

The panel member 16 may be formed by any one selected from a group consisting of flexible and resilient materials such as a paper sheet, a fibrous sheet, a foamed plastic sheet and a non-foamed plastic sheet or a laminate comprising at least two selected from this group. In general, the panel member 16 has a Gurley stiffness value of 100~250 mg, and preferably of 130~220 mg. The panel member 16 is hydrophobic and free from resilience loss and can induce a desired deformation of the core 8 even when wetted with body fluids such as menstrual discharge. The absorbent means 1, particularly the core 8 thereof generally has a Gurley stiffness value of 50~100 mg, preferably of 60~90 mg. The core 8 and the panel member 16 integrally bonded together have a Gurley stiffness value of 5~80 mg, preferably less than 60 mg when this assembly is deformed around the deformation guiding means 14, 18 towards the bottom surface of the panel member 16.

Figure 4:
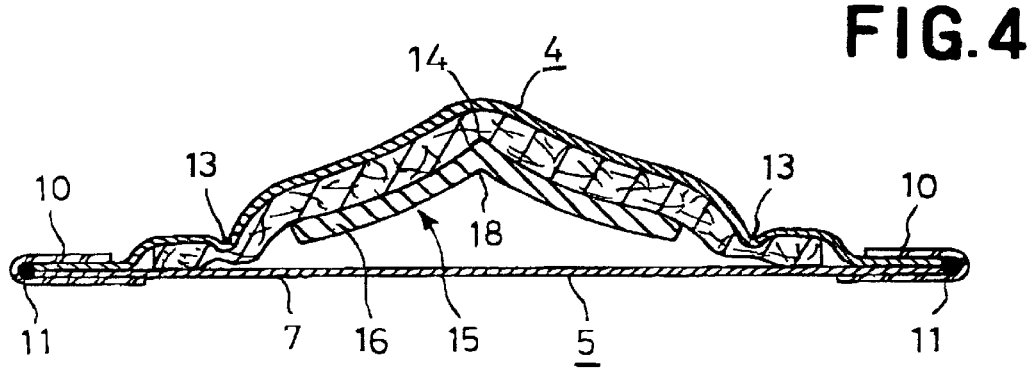
FIG. 4 is a view similar to FIG. 3 showing another embodiment of the napkin.

Referring to FIG. 4, the panel member 16 has its transversely opposite side edges lying inside the deformation guiding means 13, respectively, and bonded to the backsheet 7 by means of hot melt adhesive (not shown). Such adhesive bonding may be replaced by the heat-sealing technique.

Figure 5:
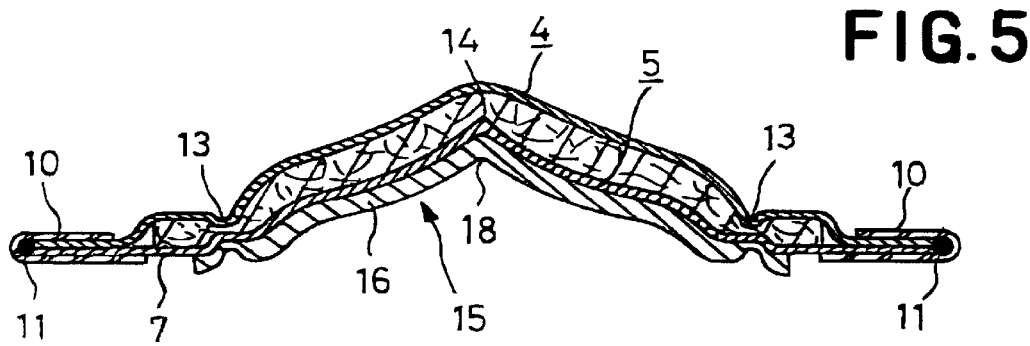
FIG. 5 is a view similar to FIG. 3 showing still another embodiment of the napkin.

Referring now to FIG. 5, the panel member 16 is bonded to an outer surface of the backsheet 7 utilizing the groups of compressed points (i.e., emboss-heat-sealing points) 13a. Such heat-sealing technique may be replaced by use of the hot melt adhesive means. The transversely opposite side edges of the panel member 16 may be located inside the deformation guiding means 13, 13, respectively. According to this embodiment also, the absorbent body 1 in the convexly deformable zone 12, i.e., the topsheet 6, the core 8 and the backsheet 7 are integrally and convexly deformed under the effect of the panel member 16.

Figure 6:
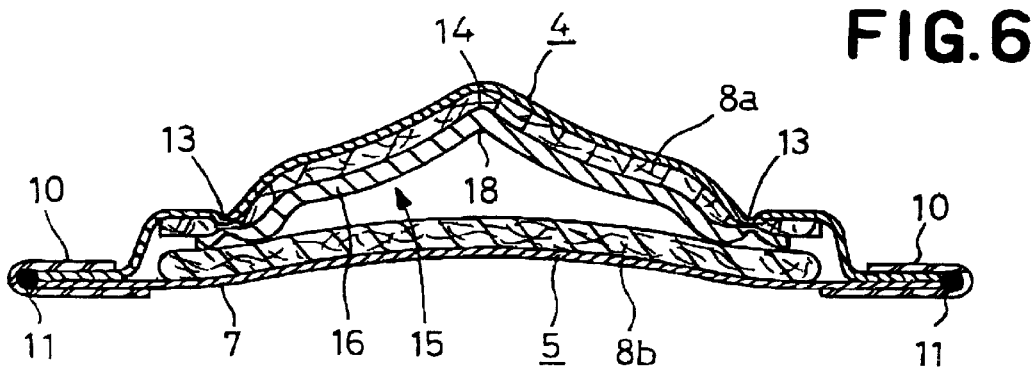
FIG. 6 is a view similar to FIG. 3 showing further another embodiment of the napkin.

Referring finally to FIG. 6, the panel member 16 is disposed between a pair of cores 8a, 8b and bonded integrally to the core 8a. In this embodiment, the panel member 16 is formed with a plurality of apertures (not shown) through which the body fluids can be absorbed by the core 8b.

The absorbent article according to the invention includes the deformation inducing means which is formed separately of the absorbent means. The deformation inducing means is placed on the garment side and has desired hydrophobic nature and rigidity to achieve its function. Specifically, even when wetted with body fluids such as menstrual discharge, the deformation inducing means causes the absorbent means in the convexly deformable zone to be convexly deformed towards the wearer's external genital organs. In this manner, fitting of said absorbent body against the wearer's external genital organs can be improved and leakage of body fluids can be reliably prevented.

The deformation inducing means comprises the hydrophobic panel member which is deformable to a substantially a flat state and causes the absorbent means in the convexly deformable zone to be convexly deformed along the contour of the wearer's external genital organs under the pressure exerted by the garment worn by the wearer. Accordingly, the article can be packaged with the absorbent means and the deformation inducing means being in their flat states.

What is claimed is:

1. An absorbent article which comprises:
    a substantially flat and elongate structure having a longitudinal center line, a transverse center line being orthogonal to said longitudinal center line, a body-facing side and a garment-facing side;
    an absorbent pad;
    deformation inducing means lying adjacent said garment-facing side for causing said absorbent pad to be convexly deformed towards the body-facing side, said deformation inducing means comprising a hydrophobic panel member having a Gurley stiffness value of at least 100 mg; and
    a first deformation guiding means provided at a convexly deformable zone of said absorbent pad and said panel member, said first deformation guiding means being formed on said garment-facing side so as to lie on transversely opposite sides of said absorbent pad symmetrically with respect to said longitudinal center line and, in said convexly deformable zone, to extend along said longitudinal center line.

2. The article according claim 1, wherein said first deformation guiding means comprises a member selected from the group consisting of creases, slits, and compressed points.

3. The article according to claim 1, wherein said convexly deformable zone of said absorbent pad includes second deformation guiding means which extend adjacent to at least transversely opposite side edges of a contour line which defines said convexly deformable zone.

4. The article according to claim 3, wherein said second deformation guiding means comprises a member selected from the group consisting of compressed points and creases.

5. The article according to claim 1, wherein said panel member is resilient.

6. The article according to claim 1, wherein said absorbent pad and said panel member are integrally bonded together along opposed surfaces thereof and the resulting bonded structure has a maximum Gurley stiffness value of 75 mg when said structure is deformed around said first deformation guiding means towards a bottom surface of said panel member.

7. The article according to claim 1, wherein said panel member is formed from a member selected from a group consisting of a paper sheet, a fibrous sheet, a foamed plastic sheet, a non-foamed plastic sheet, and a laminate of combinations thereof.

8. The article according to claim 1, wherein said absorbent pad comprises:

a liquid-pervious topsheet;

a liquid-impervious backsheet; and a liquid-absorbent core disposed between said liquid-pervious topsheet and said liquid-impervious backsheet.

9. The article according to claim 8, wherein, at least in said convexly deformable zone, surfaces of said liquid-absorbent core and said liquid-impervious backsheet opposed to each other are not integrally bonded together so that these opposed surfaces can be spaced apart from each other.

10. The article according to claim 8, wherein said deformation inducing means is disposed between said liquid-absorbent core and said liquid-impervious backsheet.

11. The article according to claim 8, wherein said deformation inducing means lies on an outer surface of said liquid-impervious backsheet.

* * * * *